(12) United States Patent
Chandrashekarappa et al.

(10) Patent No.: US 8,798,228 B2
(45) Date of Patent: Aug. 5, 2014

(54) METHOD TO REDUCE RADIATION DOSE DELIVERED BY IMAGING SYSTEM

(75) Inventors: Arun Kumar Chandrashekarappa, Bangalore (IN); Pankaj Giri, Bangalore (IN); Gobinath Mani, Bangalore (IN); Yasuhiro Imai, Waukesha, WI (US); Haruna Onodera, Hino (JP)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 13/409,912

(22) Filed: Mar. 1, 2012

(65) Prior Publication Data

US 2012/0224665 A1 Sep. 6, 2012

(30) Foreign Application Priority Data

Mar. 3, 2011 (IN) .............................. 627/CHE/2011

(51) Int. Cl.
*A61B 6/03* (2006.01)
(52) U.S. Cl.
USPC ................................................. 378/16; 378/4
(58) Field of Classification Search
USPC ....................................................... 378/4, 16
See application file for complete search history.

(56) References Cited

U.S. PATENT DOCUMENTS

| | | | | |
|---|---|---|---|---|
| 5,103,469 A * | 4/1992 | Tanaka | ............................. | 378/16 |
| 5,379,333 A * | 1/1995 | Toth | ................. | 378/16 |
| 5,400,378 A * | 3/1995 | Toth | ................. | 378/16 |
| 5,450,462 A * | 9/1995 | Toth et al. | ........................ | 378/16 |
| 5,485,494 A * | 1/1996 | Williams et al. | ................ | 378/16 |
| 5,657,235 A | 8/1997 | Liebmann et al. | | |
| 6,373,916 B1 * | 4/2002 | Inoue et al. | ........................ | 378/4 |
| 6,490,337 B1 * | 12/2002 | Nagaoka et al. | ................ | 378/20 |
| 7,313,224 B1 | 12/2007 | Saunders | | |
| 7,627,079 B2 | 12/2009 | Boone et al. | | |
| 2002/0080912 A1 * | 6/2002 | Mackie et al. | .................. | 378/21 |
| 2002/0085672 A1 | 7/2002 | Ganin et al. | | |
| 2003/0016778 A1 * | 1/2003 | Tachizaki et al. | ................. | 378/4 |
| 2004/0062341 A1 * | 4/2004 | Popescu et al. | ................... | 378/4 |
| 2004/0086076 A1 * | 5/2004 | Nagaoka et al. | .................. | 378/4 |
| 2005/0185759 A1 * | 8/2005 | Toth et al. | ..................... | 378/109 |
| 2005/0185760 A1 * | 8/2005 | Suzuki | .......................... | 378/109 |

(Continued)

FOREIGN PATENT DOCUMENTS

| | | | |
|---|---|---|---|
| EP | 1216661 A2 | 6/2002 | |
| EP | 2130491 A1 | 12/2009 | |

(Continued)

OTHER PUBLICATIONS

Lee, C.H. et al., "Radiation Dose Modulation Techniques in the Multidetector CT Era: From Basics to Practice", Radiographics, vol. 28, No. 5, Sep. 1, 2008 pp. 1451-1459.

(Continued)

*Primary Examiner* — Hoon Song
(74) *Attorney, Agent, or Firm* — Global Patent Operation; Mark A. Conklin (57) ABSTRACT

In one embodiment, a method to reduce the radiation dose delivered by an imaging system is provided. The method comprises steps of selecting a virtual mask representation based on the shape of an organ to be masked, displaying the virtual mask representation on a scout image and manipulating radiation dose to be delivered so as to modify the virtual mask representation to obtain an optimum attenuation profile.

6 Claims, 4 Drawing Sheets

(56) References Cited

U.S. PATENT DOCUMENTS

| | | |
|---|---|---|
| 2006/0018435 A1* | 1/2006 | Toth et al. .................. 378/165 |
| 2007/0116337 A1 | 5/2007 | Toth et al. |
| 2007/0147579 A1* | 6/2007 | De Man et al. ............... 378/16 |
| 2009/0016484 A1* | 1/2009 | Wang .......................... 378/19 |
| 2009/0046833 A1* | 2/2009 | Hirokawa et al. ........... 378/108 |
| 2009/0326615 A1 | 12/2009 | Nord et al. |
| 2010/0254509 A1* | 10/2010 | Sugaya et al. ............... 378/16 |

FOREIGN PATENT DOCUMENTS

| | | |
|---|---|---|
| JP | 2004321587 A | 11/2004 |
| JP | 2005312970 A | 11/2005 |
| JP | 2007020604 A | 2/2007 |
| JP | 2008220452 A | 9/2008 |
| JP | 2009009030 A | 1/2009 |
| JP | 2011045588 A | 4/2012 |
| WO | 2011/008967 A1 | 1/2011 |

OTHER PUBLICATIONS

Kalra, MK et al., "Techniques and Applications of Automatic Tube Current Modulation for CT", Radiological Society of North America, vol. 233, Jan. 1, 2004, pp. 649-657.

Search Report and Written Opinion from NL Application No. 2008400 dated Mar. 20, 2013.

* cited by examiner

METHOD TO REDUCE RADIATION DOSE DELIVERED BY IMAGING SYSTEM

FIELD OF INVENTION

This application claims priority to and the benefit of prior-filed, co-pending Indian patent application serial number 627/CHE/2011, titled METHOD TO REDUCE RADIATION DOSE DELIVERED BY IMAGING SYSTEM, filed Mar. 3, 2011. The invention generally relates to a computed tomography (CT) imaging apparatus and more particularly to reducing the radiation dose applied to a patient during a CT scan without significantly affecting the image quality.

BACKGROUND OF THE INVENTION

Radiation exposure to patients has become a concern for the radiologist community in the multi detector computed tomography (CT) era. With the introduction of faster multi detector CT scanners, various techniques have been developed to reduce the radiation dose delivered to the patient.

Selective shielding of radiation sensitive tissues and organs during CT scanning has been described in the prior art. However, the use of products implementing this technology is not generally recommended as the radiation dose reduction the products provide can be readily achieved by decreasing x-ray tube current, which does not introduce noise or increase beam-hardening artifacts.

Another prior art suggests using shields made of thin sheets of flexible latex impregnated with bismuth and shaped to cover the eye lens, thyroid, or breasts for example, during brain, cervical spine, or chest CT exams. However, using such shields is reported to give rise to artifacts near the shields. Additionally, these shields overestimate organ dose reductions by assuming that organ doses are equivalent to the measured skin dose reductions.

Yet another prior art suggests using selective in-plane shielding. One of the problems associated with selective in-plane shielding is that, it is not cost effective and reduces the image quality.

Hence there exists a need for a method that reduces the radiation dose applied to patients during computed tomography (CT) imaging, while optimizing the image quality.

BRIEF DESCRIPTION OF THE INVENTION

The above-mentioned shortcomings, disadvantages and problems are addressed herein which will be understood by reading and understanding the following specification.

In one embodiment, a method to reduce the radiation dose delivered by an imaging system is provided. The method comprises steps of selecting a virtual mask representation based on the shape of an organ to be masked, displaying the virtual mask representation on a scout image and manipulating radiation dose to be delivered so as to modify the virtual mask representation to obtain an optimum attenuation profile.

In another embodiment, the method to reduce the radiation dose delivered by an imaging system comprises steps of selecting a virtual mask representation based on the shape of an organ to be masked, obtaining an image data set for the virtual mask representation, calculating radiation dose to be delivered as a function of the image data set, manipulating the radiation dose to be delivered so as to modify the virtual mask representation to obtain an optimum attenuation profile and controlling beam modulation depending on the virtual mask representation.

In yet another embodiment, a system to reduce radiation dose delivered by an imaging system is provided. The system comprises a display unit configured for displaying a scout image along with a virtual mask representation selected by a user and a processing unit coupled to the display unit. The processing unit is configured for performing beam modulation based on the virtual mask representation such that the beam modulation affects the radiation dose delivered by an imaging system. The processing unit comprises a selection module for selecting scanning parameters based on the virtual mask representation displayed on the scout image and a control module for using the scanning parameters to provide control signals to a source controller and a gantry motor controller so as to perform beam modulation based on the virtual mask representation.

Systems and methods of varying scope are described herein. In addition to the aspects and advantages described in this summary, further aspects and advantages will become apparent by reference to the drawings and with reference to the detailed description that follows.

DETAILED DESCRIPTION OF THE INVENTION

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

A general computed tomography (CT) system has a radiation source which projects a collimated, fan-shaped beam through a patient towards a bank of radiation detectors. The source and detectors are placed on a gantry that rotates around the patient. The patient table can be shifted inside the gantry, or translated. The angle and position at which the x-ray beam intersects the body can be continuously modified. Each detector produces a signal that is a measure of the body's global transparency from the source down to the detector. The set of detectors' values acquired for a particular source position is referred as a "projection". A "scan" comprises a set of projections made at different gantry or table positions. The CT system acquires many projections during 360 degree gantry rotation around the patient in order to build a two dimensional image or "slice" through the body. Some of the CT systems build many slices simultaneously by using multiple rows of detectors. For every projection a reference detector measures the unattenuated beam intensity. This reference data is used in subsequent processing of the x-ray projection data to normalize it to a common reference dose.

This method collects the data for a complete gantry rotation with the patient in a fixed position. Between successive slices the patient is moved to a new position where the next slice can be scanned. This process continues until all planned slices have been scanned. The slice wise image data collection from the patient is used to produce CT images.

Figure 1:
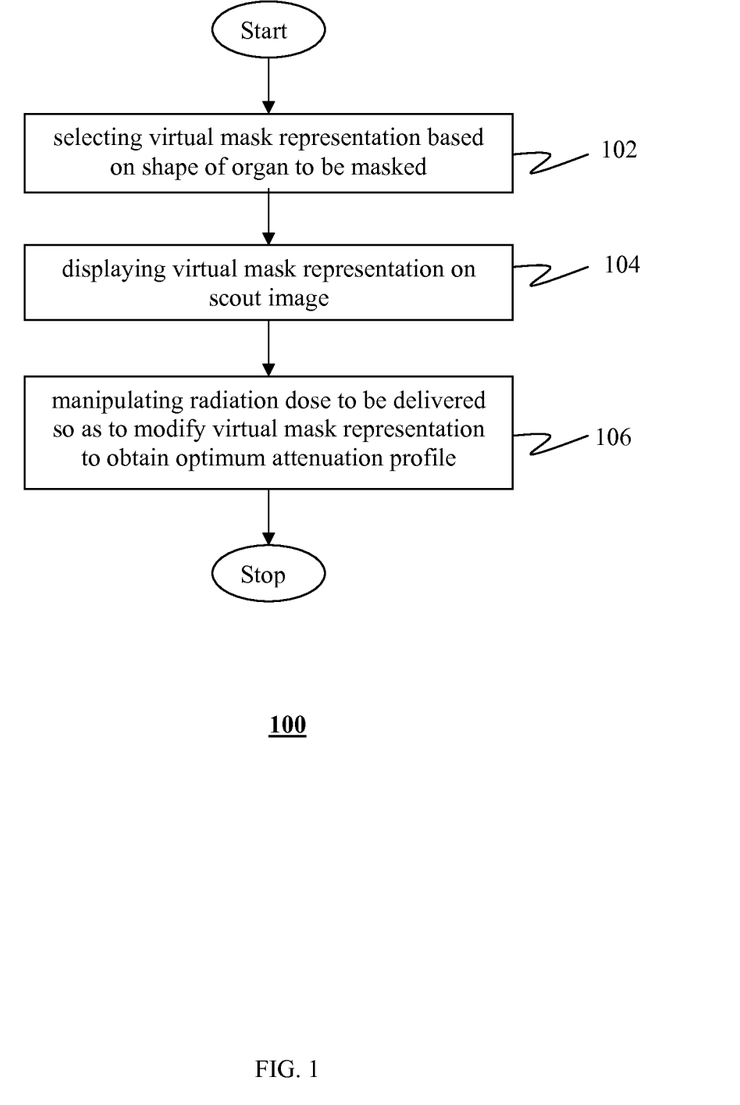
FIG. 1 shows a flow diagram depicting a method of reducing radiation dose delivered by an imaging system, as described in an embodiment of the invention.

In one embodiment, as shown in FIG. 1, a method 100 of reducing the radiation dose delivered by the CT imaging system is provided. The method 100 comprises steps of selecting a virtual mask representation based on the shape of an organ to be masked at step 102, displaying the virtual mask representation on a scout image at step 104 and manipulating radiation dose to be delivered so as to modify the virtual mask representation to obtain an optimum attenuation profile at step 106.

Displaying the virtual mask representation on the scout image allows the user to see exactly where an image shall be constructed from with respect to the patient anatomy. The area or region covered by the virtual representation mask can be used to generate control signals used to provide beam modulation thereby varying x-ray radiation per rotation angle.

Accordingly, the method 100 further comprises controlling beam modulation depending on the virtual mask representation. Beam modulation works by changing the output of the x-ray tube during the CT scan as the effective thickness of the patient changes. For example, less radiation is needed to penetrate the lung fields (due to the low density of the lungs), while higher radiation levels are needed to penetrate the thicker abdomen.

Figure 2:
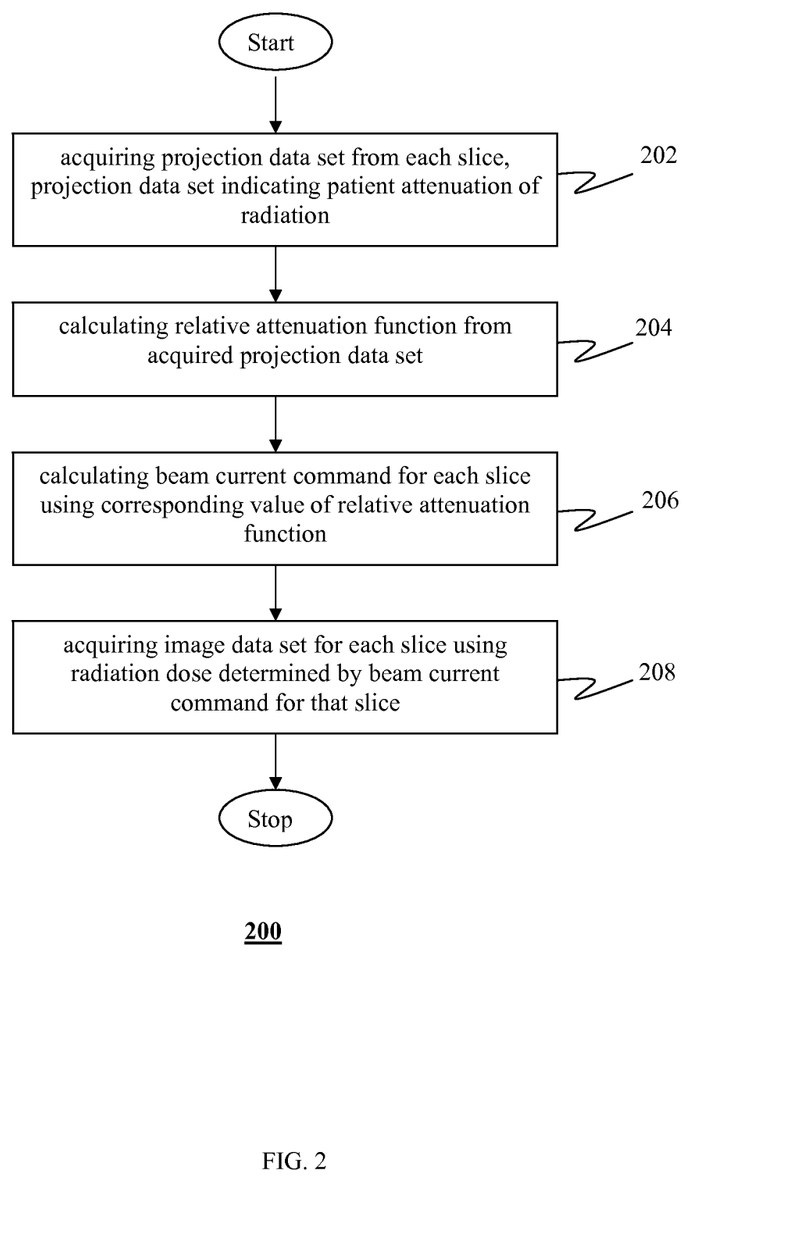
FIG. 2 shows a flow diagram depicting a method of manipulating radiation dose to be delivered, as described in FIG. 1.

FIG. 2 describes the step 106 shown in FIG. 1. Accordingly, in one embodiment, the method 200 of manipulating the radiation dose comprises steps of acquiring projection data set from each slice, the projection data set indicating patient attenuation of the radiation at step 202, calculating a relative attenuation function from acquired projection data set, the relative attenuation function indicating the expected radiation attenuation at each slice location relative to the radiation attenuation of a known reference object at step 204, calculating a beam current command for each slice using the corresponding value of the relative attenuation function and a reference beam current command that produces the desired radiation dose in the known reference object at step 206 and acquiring image data set for each slice using the radiation dose determined by the beam current command for that slice at step 208.

The image data set can be used to compute the radiation dose to each patient on an individualized basis, as long as some basic information is known about the configuration of the CT scanner and its x-ray output properties. Furthermore, because the CT image data contains information regarding the patient's shape in both θ and the z-axis, the dose can be computed taking into consideration the θ and z-axis modulation that most scanners employ.

The method described herein allows the radiologist to treat a patient from multiple angles while varying the shape and dose of the radiation beam, thereby providing greatly enhanced ability to deliver radiation to a target organ while avoiding excess irradiation of nearby healthy tissue or sensitive organs.

Figure 3:
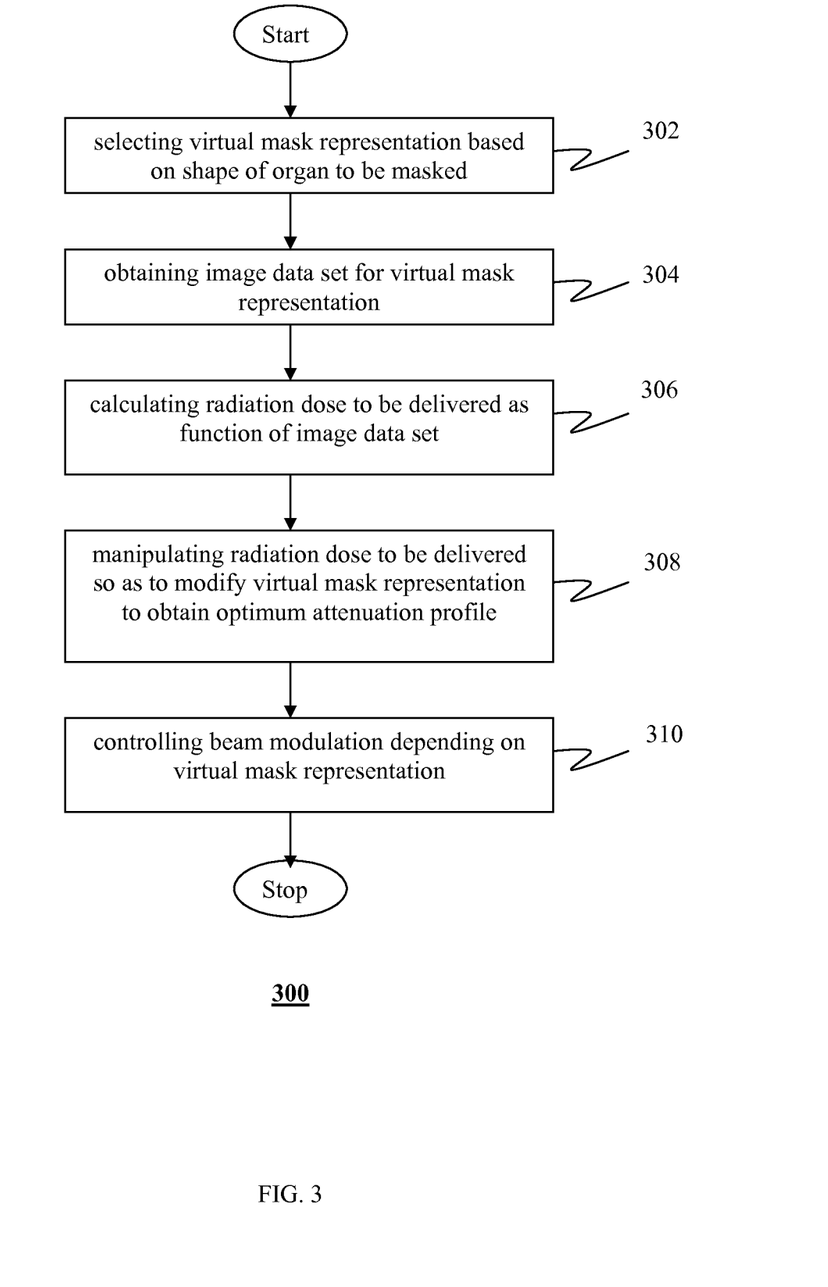
FIG. 3 shows a flow diagram depicting a method of reducing radiation dose delivered by an imaging system, as described in another embodiment of the invention.

In yet another embodiment, as shown in FIG. 3, another method 300 to reduce the radiation dose delivered by an imaging system is described. The method 300 comprises steps of selecting a virtual mask representation based on the shape of an organ to be masked at step 302, obtaining an image data set for the virtual mask representation at step 304, calculating radiation dose to be delivered as a function of the image data set at step 306, manipulating the radiation dose to be delivered so as to modify the virtual mask representation to obtain an optimum attenuation profile at step 308 and controlling beam modulation depending on the virtual mask representation at step 310.

Figure 4:
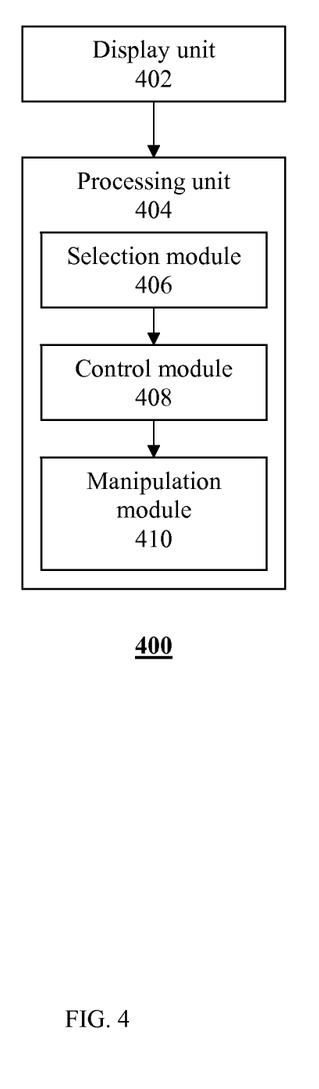
FIG. 4 shows a block diagram showing a system for reducing radiation dose delivered by an imaging system, as described in an embodiment of the invention.

In yet another embodiment shown in FIG. 4, a system 400 to reduce radiation dose delivered by an imaging system is provided. The system 400 comprises a display unit 402 configured for displaying a scout image along with a virtual mask representation selected by a user, the scout image displaying the location of the image to be constructed with respect to the patient anatomy and a processing unit 404 coupled to the display unit 402. The processing unit 404 is configured for performing beam modulation based on the virtual mask representation such that the beam modulation controls the radiation dose delivered by the imaging system. The processing unit 404 comprises a selection module 406 for selecting scanning parameters based on the virtual mask representation displayed on the scout image and a control module 408 for using the scanning parameters to provide control signals to a source controller and a gantry motor controller so as to perform beam modulation based on the virtual mask representation. The processing unit 404 further comprises a manipulation module 410 configured for manipulating the radiation dose to be delivered so as to modify the virtual mask representation to obtain an optimum attenuation profile The rotation of the gantry and the operation of the radiation source are governed by a control mechanism of the CT system. The control mechanism includes a source controller that provides power and timing signals to the radiation source and a gantry motor controller that controls the rotational speed and position of the gantry. A data acquisition system (DAS) in the control mechanism samples analog data from detector elements and converts the data to digital signals for subsequent processing. An image reconstructor, receives sampled and digitized x-ray data from the DAS and performs high speed image reconstruction. The reconstructed image is applied as an input to a computer, which stores the image in a mass storage device.

The computer is operably coupled to the processing unit 404 that receives commands and scanning parameters from an operator via console that has a keyboard. An associated display unit 402 allows the operator to observe the reconstructed image and other data from the processing unit 404. The operator supplied commands and parameters are used by the processing unit 404 to provide control signals and information to the DAS, the source controller and the gantry motor controller. In addition, processing unit 404 operates a table motor controller, which controls a motorized table to position the patient in the gantry.

In one embodiment, the scout image is displayed on the display unit 402. The virtual mask representation is displayed on the scout image. The scanning parameters are selected based on the virtual mask representation displayed on the scout image. The scanning parameters are used by the processing unit 404 to provide control signals and information to the source controller and gantry motor controller. The control signals include current (mA) modulation in the radiation beam that influences the radiation dose that is to be delivered to the patient.

Referring particularly to FIG. 4, the processing unit 404 directs the imaging system components to carry out a prescribed scan in accordance with stored programs. The first step is to acquire scout data. The scout data comprises two orthogonal views from each slice in the prescribed scan, one at a gantry angle of 0.degree and the other at an angle of 90.degree.

For each slice, a relative attenuation value RAF is calculated, and together these define a relative attenuation function, which indicates the x-ray attenuation expected at each slice in the scan. The relative attenuation values may be determined using a number of methods that are known to those skilled in the art. Also, the patient projection data is acquired using a scout scan.

The next step in the process is to calculate tube current commands mA for each slice in the scan using the RAF values. Once the scan is started, the system remains in a loop until the last slice has been acquired. For each slice, the processing unit 404 downloads the calculated current command mA to the source controller, and directs the control mechanism to acquire the attenuation data for one slice. This cycle is repeated for each slice in the scan with the x-ray dose for each slice being governed by the calculated current command mA for the slice. For example, for slices acquired through the patient's lungs the current command will be relatively low, whereas it will be high for slices through the patient's hips. The method described herein maintains the image quality throughout the scan.

The resulting current commands are checked to insure none exceed the upper or lower limits of the source controller. If any do, they can be set to the controller limit or the operator may be signaled. The scout data may also be used to determine if any signals during the scan will be insufficient in magnitude, or will be too large and will over range the detector channels.

If the result is greater than the upper limit, the mA would be reduced and/or the technologist would be notified. The upper limit is the maximum signal that the DAS can measure minus some design margin.

If the signal is less than the minimum limit, the user is notified that a significant image quality noise improvement can be achieved if the exam kV and/or slice thickness are increased. The minimum limit is a predetermined point where the ratio of total noise in the raw signal relative to the quantum noise in the raw signal is greater than 1.1.

Also, x-ray tube heating can be predicted based on the current commands (mA). If problems are found, mA commands can be changed for those slices where the signal (dose) is highest before the scan is performed.

The system and method to reduce radiation dose delivered by an imaging system as described in various embodiments of the invention provide a number of advantages. In one embodiment, the method increases the modulation of the radiation beam generated by the imaging system. Generally, increased modulation is associated with better dose distribution in the irradiated area. Specifically, increased modulation generally allows better protection of healthy tissue in the irradiated area and also allows better dose distribution in the target organ.

The method described herein allows the user to graphically view and modify the virtual mask representation. Modification of the virtual mask representation can be carried out until it matches the shape of the organ to be masked. Subsequent to this the user can accurately place the virtual mask representation of the sensitive organ.

In one embodiment, the method enables the user to view the modifications carried on the virtual mask representation on both AP (antero-posterior) and lateral scouts.

This written description uses examples to describe the subject matter herein, including the best mode, and also to enable any person skilled in the art to make and use the subject matter. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method to reduce the radiation dose delivered by an imaging system, the method comprising:
    a user selecting a virtual mask representation based on the shape of an organ to be masked;
    displaying, the virtual mask representation on a scout image;
    manipulating radiation dose to be delivered so as to modify the virtual mask representation to obtain an optimum attenuation profile; and wherein
    the step of manipulating radiation dose comprises:
        acquiring a projection data set from each slice the virtual mask, the projection data set indicating patient attenuation of the radiation;
        calculating a relative attenuation function from the acquired projection data set, the relative attenuation function indicating the expected radiation attenuation at each slice location relative to the radiation attenuation of a known reference object;
        calculating a beam current command for each slice using the corresponding value of the relative attenuation function and a reference beam current command that produces the desired radiation dose in the known reference object;
        acquiring image data set for each slice using the radiation dose determined by the beam current command for that slice; and wherein
        the method allowing the user to treat a patient from multiple angles while varying the shape and dose of the radiation beam and thereby deliver radiation to a target while avoiding excess irradiation of the masked organ.

2. The method of claim 1, further comprising:
    controlling beam modulation depending on the virtual mask representation.

3. The method of claim 1, further comprising displaying the radiation dose delivered.

4. The method of claim 1, wherein optimum attenuation profile is selected based on a minimum radiation dose delivered to the masked organ.

5. The method of claim 1, wherein optimum attenuation profile indicates a dose match between the virtual mask representation and an ideal image of the organ to be masked.

6. A system to reduce radiation dose delivered by an imaging system, the system comprising:
    a display unit configured for displaying a scout image along with a virtual mask representation selected by a user, the scout image displaying the location of the image to be constructed with respect to the patient anatomy;
    a processing unit coupled to the display unit, the processing unit configured for performing beam modulation based on the virtual mask representation such that the beam modulation controls the radiation dose delivered by the imaging system, the processing unit comprising:
        a selection module for selecting scanning parameters based on the virtual mask representation displayed on the scout image;
        a control module for using the scanning parameters to provide control signals to a source controller and a gantry motor controller so as to perform beam modulation based on the virtual mask representation; and a manipulation module for carrying out the beam modulation including the steps of:

acquiring projection data set from each slice of a plurality of slices of the virtual mask, the projection data set indicating patient attenuation of the radiation; and calculating a relative attenuation function from acquired projection data set, the relative attenuation function indicating the expected radiation attenuation at each slice location relative to the radiation attenuation of a known reference object;

calculating a beam current command for each slice using the corresponding value of the relative attenuation function and a reference beam current command that produces the desired radiation dose in the known reference object;

acquiring image data set for each slice using the radiation dose determined by the beam current command for that slice; and the system allowing the user to treat a patient from multiple angles while varying the shape and dose of the radiation beam and thereby deliver radiation to a target organ while avoiding excess irradiation of nearby tissue or other organs.

* * * * *

UNITED STATES PATENT AND TRADEMARK OFFICE
CERTIFICATE OF CORRECTION

PATENT NO.       : 8,798,228 B2
APPLICATION NO.  : 13/409912
DATED            : August 5, 2014
INVENTOR(S)      : Chandrashekarappa et al.

It is certified that error appears in the above-identified patent and that said Letters Patent is hereby corrected as shown below:

In the Claims

In Column 6, Line 13, in Claim 1, delete "displaying," and insert -- displaying --, therefor.

In Column 6, Line 49, in Claim 5, delete "a dose" and insert -- a close --, therefor.

Signed and Sealed this
Twenty-sixth Day of May, 2015

Michelle K. Lee
*Director of the United States Patent and Trademark Office*